United States Patent
Virmani et al.

(10) Patent No.: US 10,076,541 B2
(45) Date of Patent: Sep. 18, 2018

(54) COMPOSITION USEFUL AS A DIETARY SUPPLEMENT

(71) Applicant: SIGMA-TAU Industrie Farmaceutiche Riunite S.p.A., Rome (IT)

(72) Inventors: Ashraf Virmani, Rome (IT); Safouane Zerelli, Utrech (NL)

(73) Assignee: SIGMA-TAU INDUSTRIE FARMACEUTICHE RIUNITE S.P.A., Rome (IT)

( * ) Notice: Subject to any disclaimer, the term of this patent is extended or adjusted under 35 U.S.C. 154(b) by 0 days.

(21) Appl. No.: 15/101,442

(22) PCT Filed: Nov. 13, 2014

(86) PCT No.: PCT/EP2014/074424
§ 371 (c)(1),
(2) Date: Jun. 3, 2016

(87) PCT Pub. No.: WO2015/082180
PCT Pub. Date: Jun. 11, 2015

(65) Prior Publication Data
US 2016/0303164 A1    Oct. 20, 2016

(30) Foreign Application Priority Data

Dec. 5, 2013 (EP) ..................... 13195774

(51) Int. Cl.
| | | |
|---|---|---|
| A23L 33/15 | (2016.01) | |
| A61K 33/34 | (2006.01) | |
| A61K 45/06 | (2006.01) | |
| A61K 31/07 | (2006.01) | |
| A61K 31/195 | (2006.01) | |
| A61K 31/198 | (2006.01) | |
| A61K 31/205 | (2006.01) | |
| A61K 31/355 | (2006.01) | |
| A61K 31/375 | (2006.01) | |
| A61K 31/4415 | (2006.01) | |
| A61K 31/525 | (2006.01) | |
| A61K 31/592 | (2006.01) | |
| A61K 31/593 | (2006.01) | |
| A61K 31/714 | (2006.01) | |
| A61K 33/04 | (2006.01) | |
| A61K 33/26 | (2006.01) | |
| A61K 33/30 | (2006.01) | |
| A23L 33/155 | (2016.01) | |
| A23L 33/16 | (2016.01) | |
| A23L 33/175 | (2016.01) | |
| A23L 33/10 | (2016.01) | |
| A23L 33/00 | (2016.01) | |
| A61K 9/00 | (2006.01) | |
| A61K 31/197 | (2006.01) | |
| A61K 31/519 | (2006.01) | |
| A61K 31/59 | (2006.01) | |

(52) U.S. Cl.
CPC .............. *A61K 33/34* (2013.01); *A23L 33/10* (2016.08); *A23L 33/15* (2016.08); *A23L 33/155* (2016.08); *A23L 33/16* (2016.08); *A23L 33/175* (2016.08); *A23L 33/40* (2016.08); *A61K 9/0053* (2013.01); *A61K 31/07* (2013.01); *A61K 31/195* (2013.01); *A61K 31/197* (2013.01); *A61K 31/198* (2013.01); *A61K 31/205* (2013.01); *A61K 31/355* (2013.01); *A61K 31/375* (2013.01); *A61K 31/4415* (2013.01); *A61K 31/519* (2013.01); *A61K 31/525* (2013.01); *A61K 31/59* (2013.01); *A61K 31/592* (2013.01); *A61K 31/593* (2013.01); *A61K 31/714* (2013.01); *A61K 33/04* (2013.01); *A61K 33/26* (2013.01); *A61K 33/30* (2013.01); *A61K 45/06* (2013.01); *A23V 2002/00* (2013.01)

(58) Field of Classification Search
CPC ........ A23L 33/40; A23L 33/155; A23L 33/15; A61K 33/34; A61K 33/30; A61K 31/198
USPC .......................................... 514/5.5
See application file for complete search history.

(56) References Cited

U.S. PATENT DOCUMENTS

2007/0104801 A1   5/2007 Cecchi et al.
2009/0170858 A1*  7/2009 Bailey .................. A61K 8/4953
                                                    514/249

FOREIGN PATENT DOCUMENTS

| EP | 1 714 658 A1 | 10/2006 |
| WO | WO 03/086080 A1 | 10/2003 |
| WO | WO 2012/076680 A1 | 6/2012 |

OTHER PUBLICATIONS

Anonymous. Carnitine; NIH Office of Dietary Supplements, pp. 1-4, downloaded from https://ods.od.nih.gov/factsheets/Carnitine-HealthProfessional/ on Feb. 6, 2018. (Year: 2018).*

(Continued)

*Primary Examiner* — Scott Long
*Assistant Examiner* — Paul C Martin
(74) *Attorney, Agent, or Firm* — Sterne, Kessler, Goldstein & Fox P.L.L.C.

(57) ABSTRACT

Compositions comprising L-carnitine or a salt thereof, acetyl L-carnitine or a salt thereof, vitamin B9 (folic Acid), vitamin A, vitamin B12, vitamin B5 (pantothenic acid), vitamin B6 (pyridoxine), arginine, vitamin C, vitamin E (α-Tocopherol), selenium, zinc, copper, iron, vitamin D and N-acetyl cysteine, and optionally one or more pharmaceutically acceptable excipients are provided. Dietary supplements comprising these compositions are also provided.

16 Claims, No Drawings

(56) References Cited

OTHER PUBLICATIONS

Anonymous. L-Carnitine; Linus Pauling Institute Micronutrient Information Center, pp. 1-37 downloaded from http://www.lpi.oregonstate.edu/mic/dietary-factors/L-carnitine on Feb. 6, 2018. (Year: 2018).*
International Search Report for International Application No. PCT/EP2014/074424, filed Nov. 13, 2014, European Patent Office, Netherlands, dated Jan. 22, 2015.
Written Opinion for International Application No. PCT/EP2014/074424, filed Nov. 13, 2014, European Patent Office, Netherlands, dated Jan. 22, 2015.

* cited by examiner

COMPOSITION USEFUL AS A DIETARY SUPPLEMENT

FIELD OF THE INVENTION

The field of this invention relates to female fertility during hormonal or pharmacological stimulation.

BACKGROUND OF THE INVENTION

Female Infertility affects about 48 million women around the world.

About 10 percent of reproductive-age couples in the United States have difficulty getting pregnant.

Stimulating ovulation with fertility hormones or drugs is the main treatment for women who are infertile due to ovulation disorders, these medications regulate or induce ovulation.

Drugs useful for stimulating ovulation are:

Clomiphene citrate: this drug causes ovulation by acting on the pituitary gland. It is often used in women who have Polycystic Ovarian Syndrome (PCOS) or other problems with ovulation. Clomiphene citrate acts as a fertility agent in women by inducing superovulation, i.e. the release of multiple eggs in a given menstrual cycle. This medicine is taken by mouth.

Bromocriptine and Cabergoline: these drugs are used to reduce the amount of prolactin released by the pituitary in women with ovulation problems due to high levels of prolactin. Potential side effects include nausea, vomiting, nasal congestion, headache, dizziness, fainting, and decreased blood pressure.

Medrol: a steroid provided daily for four days during the cycle to assist with pre-embryo implantation.

Injectable hormones used for stimulating ovulation are:

Human Chorionic Gonadotropin (hCG) usually in combination with other fertility drugs and nutritional supplement, to trigger the ovaries to release the mature egg or eggs;

Follicle Stimulating Hormone (FSH);

Human Menopausal Gonadotropin (hMG). This drug combines both FSH and LH (luteinizing hormone).

Gonadotropin Releasing Hormone (GnRH. This hormone stimulates the release of FSH and LH from the pituitary gland. These hormones are rarely prescribed in the U.S.

Gonadotropin Releasing Hormone Agonist (GnRH agonist);

Gonadotropin Releasing Hormone Antagonist (GnRH antagonist).

All these drugs/hormones can be used for increasing oocyte fertilization in vivo or in vitro.

In vitro fertilisation (IVF) is a process by which oocyte is fertilised by sperm outside the body: in vitro. IVF is a major treatment for infertility when other methods of assisted reproductive technology have failed. The process involves monitoring and stimulating a woman's ovulatory process, removing oocyte or oocytes from the woman's ovaries and letting sperm fertilise them in a fluid medium in a laboratory. The fertilised oocyte (zygote) cultured for 2-6 days in a growth medium is then transferred to the patient's uterus with the intention of establishing a successful pregnancy.

It is reported that fertility hormones and drugs for the primary treatment for women with ovulation disorders are endowed with side effects.

It is reported that fertility in women is affected by oxidative stress due to the exposures to alcohol, tobacco smoke and/or environmental pollutants.

In Curr Opin Obstet Gynecol. 2009 June; 21(3): 219-222 it is reported that the role of oxidative stress in female fertility is an understudied and compelling area for investigation; and that identifying modifiable factors to decrease oxidative stress in the gynecologic environment may be an inexpensive and noninvasive therapy for increasing fertility. In order to improve reproductive health of female (human or animals) it has been recommended to feed a good multivitamin preparation and include sufficient amounts of antioxidants and supplements in the diet.

Vitamin E is crucial to proper reproductive function in women, in fact, the chemical name for vitamin E, "tocopherol," originated from the Greek words tokos, which means "offspring," and phero, which means "to bear." Vitamin E protects hormones from oxidation. Vitamin E becomes less available in selenium processed foods and exposure to harmful oxidizing agents, supplementation with 400-800 IU of vitamin E daily may improve fertility.

In Fertil Steril. 2008 March; 89(3):668-76. Epub 2007 Jul. 10, it is reported that Folic acid supplementation may improve fertility in women.

In Hum Reprod. 1999 July; 14(7):1690-7, it is reported that oral L-arginine supplementation in poor responder patients may improve ovarian response, endometrial receptivity and pregnancy rate.

In Anim. Reprod. Sci. 2012 September; 134(1-2):69-75, it is reported that carnitines, in vitro or in vivo, have beneficial effects on oocytes and embryo development.

In Acta Obstet Gynecol Scand. 2007; 86(2):218-22, it is reported that N-Acetyl cysteine is proved effective in inducing or augmenting ovulation in polycystic ovary patients.

In Eur J Endocrinol. 2012 May; 166(5):765-78, it is reported that vitamin D is involved in female reproduction.

U.S. Pat. No. 6,569,857 teaches a method for increasing the possibility of conception while enhancing nutritional stores for a developing embryo or fetus prior to and during pregnancy by administering to an animal during a period commencing prior to at least two weeks before conception a specific dose of vitamin B6 and folic acid.

U.S. Pat. No. 6,861,079 teaches a fertility kit to enhance natural fertility comprising specific dose ranges of L-arginine, L-cysteine, selenium, vitamin C, vitamin E, zinc, vitamin B-6, Para-aminobenzoic acid (PABA), vitamin A, folic Acid, at least one phytoestrogen, along with several devices used in the promotion ovulation.

As reported above, the use of fertility hormones/drugs is endowed with side effects which may be mild or relevant.

Therefore, needs exist for new pharmaceutical/nutraceutical compounds/compositions useful for improving fertility in women while reducing side effects due to the use of fertility hormones/drugs.

SUMMARY OF THE INVENTION

The present invention provides a synergistic combination of bioeffective compounds for promoting female fertility. All the components have been also studied separately, to determine their individual efficacy.

In particular, the present invention relates to a synergystic composition for promoting female fertility, comprising as active ingredients L-carnitine, acetyl L-carnitine; N-acetyl cysteine, and several specific vitamins, aminoacids, antioxidants and micro elements.

DESCRIPTION OF THE INVENTION

It has now been found that a combination composition comprising as active ingredients L-carnitine or a salt thereof, acetyl L-carnitine or a salt thereof; N-acetyl cysteine; and several specific vitamins, aminoacids, antioxidants and micro elements, is endowed with a surprisingly synergistic effect for promoting female fertility during drug and/or hormonal stimulation.

It is therefore one object of the present invention a combination composition comprising as active ingredients L-carnitine or a salt thereof, acetyl-L-carnitine or a salt thereof, vitamin B9 (folic Acid), vitamin A, vitamin B12, vitamin B5 (pantothenic acid), vitamin B6 (pyridoxine), arginine, vitamin C, vitamin E (α-Tocopherol), selenium, zinc, copper, iron, vitamin D and N-acetyl cysteine.

The compositions mentioned above may further comprise diluents and/or excipient, and/or further active ingredients, useful for promoting female fertility.

It is a further object of the present invention a composition comprising:

(a) L-carnitine fumarate, in a dose of from 2589 to 287.6 mg (corresponding to 1500-166.6 mg L-carnitine inner salt), the preferred doses is from 1726 to 431.5 mg (corresponding to 1000-250 mg of L-carnitine inner salt), the most preferred dose is 863 mg (corresponding to 500 mg of L-carnitine inner salt);

(b) acetyl-L-carnitine in a dose of from 750 to 25.0 mg, the preferred doses is from 500 to 125 mg, the most preferred dose is 250 mg;

(c) folic Acid (vitamin B9) in a dose of from 600 to 66.6 mcg, the preferred doses is from 400 to 100 mcg, the most preferred dose is 200 mcg;

(d) vitamin A from Beta Carotene in a dose of from 2400 to 266.6 mcg, the preferred doses is from 1600 to 400 mcg, the most preferred dose is 800 mcg;

(e) vitamin B12 in a dose of from 7.5 to 0.833 mcg, the preferred doses is from 5.0 to 1.250 mcg, the most preferred dose is 2.5 mcg;

(f) vitamin B5 (pantothenic) in a dose of from 18.0 to 2.0 mg, the preferred doses is from 12.0 to 3.0 mg, the most preferred dose is 6 mg;

(g) vitamin B6 (pyridoxine) in a dose of from 6.0 to 0.666 mg, the preferred doses is from 4.0 to 1.0 mg, the most preferred dose is 2 mg;

(h) arginine in a dose of from 1500 to 166.6 mg, the preferred doses is from 1000.0 to 250.0 mg, the most preferred dose is 500 mg;

(i) vitamin C in a dose of from 270.0 to 30.0 mg, the preferred doses is from 180.0 to 45.0 mg, the most preferred dose is 90 mg;

(j) vitamin E (α-Tocopherolo) in a dose of from 90.0 to 10.0 mg, the preferred doses is from 60.0 to 15.0 mg, the most preferred dose is 30 mg;

(k) selenium in a dose of from 150 to 16.6 mcg, the preferred doses is from 100.0 to 25.0 mcg, the most preferred dose is 50 mcg;

(l) zinc in a dose of from 30.0 to 3.33 mg, the preferred doses is from 20.0 to 5.0 mg, the most preferred dose is 10 mg;

(m) copper in a dose of from 4.95 to 0.55 mg, the preferred doses is from 3.3 to 0.825 mg, the most preferred dose is 1.65 mg;

(n) iron in a dose of from 42.0 to 4.66 mg, the preferred doses is from 28.0 to 7.0 mg, the most preferred dose is 14 mg;

(o) vitamin D in a dose of from 15.0 to 1.66 mcg, the preferred doses is from 10.00 to 2.50 mcg, the most preferred dose is 5 mcg;

(p) N-acetyl cysteine in a dose of from 150 to 16.6 mg, the preferred doses is from 100.0 to 25.0 mg, the most preferred dose is 50 mg.

It is a further object of the present invention the composition mentioned above, for use in promoting female fertility.

It is a further object of the present invention the composition mentioned above, for use in promoting female fertility in association with drug and/or hormonal stimulation.

It is a further object of the present invention the composition mentioned above, for use in promoting female fertility in association with drug and/or hormonal stimulation for supporting ovulation.

It is a further object of the present invention the composition mentioned above, for use in promoting female fertility during drug and/or hormonal stimulation for supporting oocyte fertilization.

It is a further object of the present invention the composition mentioned above, for use in promoting female fertility during drug and/or hormonal stimulation for promoting oocyte fertilization in vivo.

It is a further object of the present invention the composition mentioned above, for use in promoting female fertility during drug and/or hormonal stimulation for promoting oocyte fertilization in vitro.

It is a further object of the present invention the composition mentioned above, for use in reducing side effects due to the use of hormones and/or drugs useful for promoting female fertility.

The composition of the invention can be administered to a subject in need thereof at least a month before the beginning of the drug and/or hormonal stimulation; said administration has to be started at least a week before the beginning of the drug and/or hormonal stimulation; said administration can be continued after the oocyte fertilization under the physician control.

It is a further object of the present invention the use of the composition mentioned above as a dietary supplement.

The composition of the invention may further comprise co-enzymes, further mineral substances, antioxidants, vitamins, and agents useful for promoting female fertility, or assisting in treating infertility.

What is meant by salt of L-carnitine or acetyl L-carnitine is any salt of the latter with an acid that does not give rise to toxic or side effects.

Non-limiting examples of such salts are: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

A list of FDA-approved pharmaceutically acceptable salts is given in the publication Int. J. of Pharm. 33 (1986), 201-217.

L-carnitine, acetyl-L-carnitine, vitamin B9, vitamin A, vitamin B12, vitamin B5 (pantothenic acid), vitamin B6 (pyridoxine), arginine, vitamin C, vitamin E ((α-Tocopherol), selenium, zinc, copper, iron, vitamin D and N-acetyl cysteine according to the present invention can be administrated in a "co-ordinated manner". What is meant by "co-ordinated manner" of the aforesaid compounds is, indifferently, either the co-administration, i.e. the substantially concomitant or sequential supplementation of L-carnitine and at least one acetyl-L-carnitine, vitamin B9, vitamin A, vitamin B12, vitamin B5 (pantothenic acid), vitamin B6 (pyridoxine), arginine, vitamin C, vitamin E (α-Tocopherol), selenium, zinc, copper, iron, vitamin D and N-acetyl cysteine, or the administration of a composition comprising the aforesaid active ingredients in combination and in a mixture optionally further comprising one or more excipients or diluents pharmaceutically acceptable.

The following non limiting examples further illustrate the invention.

EXAMPLE 1

Materials and Methods
Animals.

CD1 mice, 60 female and 60 male; 6 weeks age; weight 16.2 g; 5 mice per group, were used for the study. Mice were allowed to acclimate for a week prior to weighing. Female mice began superovulation 2 to 3 day after achieving the correct weight. All mice were maintained under SPF conditions under a 12:12-h light:dark cycle (lights on, 0700 to 1900) at temperatures of 21 to 24° C. Mice were housed in static microisolation caging with ad libitum access to food and water.

Treatment.

All the female mice, except the "Control" group, were treated orally (0.5 ml, gastric gavage, twice a day) for 7 days (included the days in which the mice were treated with the hormones for the superovulation) with the composition of the invention (DNCO64) having the following composition:
L-carnitine fumarate 0.4 mg+
Acetyl-L-carnitine HCl. 0.12 mg+
Vitamin B12 0.0012 mcg+
Vitamin B9 0.09 mcg+
Vitamin B6 0.0009 mg+
Vitamin B5 0.003 mg+
Vitamin A 0.4 mcg+
Vitamin D 0.0022 mcg+
Selenium 0.022 mcg+
Vitamin C 0.04 mg+
Vitamin E 0.014 mg+
Zinc 0.004 mg+
Copper 0.0008 mg+
Iron 0.007 mg+
L-Arginine 0.24 mg+
N-acetyl cysteine 0.24 mg,
combination thereof, as reported in Table 1.

Superovulation and Mating.

The superovulation technique used is described in J. Am. Assoc. Lab. Anim. Sci. 2011, July 50(4); 471-478. In short, female mice were treated with 5 IU (0.1 mL intra peritoneum) of Pregnant Mares Serum Gonadotropin (PMSG). These mice received 5 IU (0.1 mL IP) of Human Chorionic Gonadotropin (HCG) 47 to 49 h after their last PMSG injection. Immediately after HCG injection, female mice were mated 1:1 to male mice. All female mice underwent this superovulation treatment.

Oocyte Collection and Analysis.

The day after mating, all female donors were euthanized by cervical dislocation and oviducts were collected from all female mice and placed into 2 mL M2 media (Sigma-Aldrich) in a 35-mm culture dish (Fisher Scientific). Each oviduct then was moved to a dish containing 2 mL M2 media (Sigma-Aldrich) and 75 μL hyaluronidase (10 mg/mL; Sigma-Aldrich), where the ampulla was torn open to release the oocytes.

After all the oviducts for that group had been processed, all of the oocytes were collected and placed into a 100-μL drop of KSOM (Millipore, Billerica Mass.) under embryo-tested mineral oil (Sigma-Aldrich) that had been equilibrated to 37° C. at 5% $CO_2$. Oocytes were allowed to incubate for 24 h, after which the drop was scored for the number of 2-cell of fertilized oocytes.

The results obtained are reported in the following Table 1.

TABLE 1

| Superovulation treatment (Groups 1-12; 5 + 5 IU PMSG + HCG) | | | |
|---|---|---|---|
| Groups (5 mice per group) | Mean no. of oocytes/ female mouse (±SE) | Mean no. of fertilized oocytes/female mouse (±SE) | |
| N° Treatment | — | — | P < |
| 1 Control (no treatment with the composition of the invention) | 29.1 ± 1.7 | 10.7 ± 1.3 | — |
| 2 Complete composition of the invention (DNC064) | 30.3 ± 1.3 | 18.5 ± 0.9 | 0.001 vs 1 |
| 3 (Carnitines) L-carnitine fumarate 0.4 mg + Acetyl-L-carnitine HCl. 0.12 mg | 30.6 ± 1.7 | 13.1 ± 1.6 | 0.05 vs 2 NS vs 1 |
| 4 (Vitamins) Vitamin B12 0.0012 mcg + Vitamin B9 0.09 mcg + Vitamin B6 0.0009 mg + Vitamin B5 0.003 mg + Vitamin A 0.4 mcg + Vitamin D 0.0022 mcg | 29.6 ± 1.3 | 12.7 ± 2.1 | 0.05 vs 2 NS vs 1 |
| 5 (Antioxidants) Selenium 0.022 mcg + Vitamin C 0.04 mg + Vitamin E 0.014 mg | 30.0 ± 1.5 | 13.6 ± 1.8 | 0.05 vs 2 NS vs 1 |
| 6 (Micro-elements) Zinc 0.004 mg + Copper 0.0008 mg + Iron 0.007 mg | 29.6 ± 1.7 | 14.0 ± 1.7 | 0.05 vs 2 NS vs 1 |
| 7 (Amino acids) L-Arginine 0.24 mg + N-acetyl cysteine 0.24 mg | 28.6 ± 2.0 | 13.9 ± 1.6 | 0.05 vs 2 NS vs 1 |
| 8 (Group 3 + Group 4) | 29.6 ± 1.8 | 13.8 ± 1.5 | 0.05 vs 2 NS vs 1 |
| 9 (3 + 5) | 29.6 ± 2.1 | 14.1 ± 1.3 | 0.05 vs 2 NS vs 1 |
| 10 (3 + 6) | 28.1 ± 1.7 | 14.0 ± 1.3 | 0.05 vs 2 NS vs 1 |
| 11 (3 + 7) | 30.3 ± 2.2 | 13.8 ± 1.5 | 0.05 vs 2 NS vs 1 |
| 12 (4 + 5 + 6 + 7) | 28.6 ± 1.7 | 13.4 ± 2.0 | 0.05 vs 2 NS vs 1 |

Statistical Analysis

The significance was calculated using the Student t-test, $p<0.05$ Values were considered to represent a significant difference.

The results reported in Table 1 show that the treatment of the invention statistically increased the number of fertilized oocytes with respect to the single components or different combination thereof.

The composition of the present invention can be administered in any suitable form for oral administration.

An example of form of administration is in a liquid, semi-liquid or solid form in sachets, pills, vials, gel or liposome.

L-carnitine and acetyl L-carnitine are known compounds and their preparation process is described in U.S. Pat. No. 4,254,053.

Vitamin A, vitamin B9, vitamin B12, vitamin B5 (pantothenic acid), vitamin B6 (pyridoxine), arginine, vitamin C, vitamin E (-Tocopherol), selenium, zinc, copper, iron, vitamin D and N-acetyl cysteine are very long time widely sold on the market for human use.

The composition according to the present invention is composed of active ingredients which are familiar to operators in the medical field and already in use.

Their procurement therefore is very easy, inasmuch as these are products which have been on the market now for a long time and are of a grade suitable for human administration.

For any compound, the therapeutically effective dose can be estimated initially either in cell culture assays or in animal models, usually mice or rats.

The animal model may also be used to determine the appropriate concentration range and route of administration. Such information can then be used to determine useful doses and routes for administration in humans.

The precise effective dose for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician.

In the following a non-limiting example of the compositions of the invention are reported.

| Composition 1 | |
|---|---|
| L-carnitine fumarate | 863 mg (500 mg L-Carnitine base) |
| acetyl-L-carnitine | 250 mg |
| folic Acid (vitamin B9) | 200 mcg |
| vitamin A from Beta Carotene | 800 mcg |
| vitamin B12 | 2.5 mcg |
| vitamin B5 (pantothenic) | 6 mg |
| vitamin B6 (pyridoxine) | 2 mg |
| arginine | 500 mg |
| vitamin C | 90 mg |
| vitamin E (α-Tocopherolo) | 30 mg |
| selenium | 50 mcg |
| zinc | 10 mg |
| copper | 1.65 mg |
| iron | 14 mg |
| vitamin D | 5 mcg |
| N-acetyl cysteine | 50 mg. |

| Composition 2 | |
|---|---|
| L-carnitine fumarate | 430 mg |
| acetyl-L-carnitine | 125 mg |
| folic Acid (vitamin B9) | 200 mcg |
| vitamin A from Beta Carotene | 800 mcg |
| vitamin B12 | 2.5 mcg |
| vitamin B5 (pantothenic) | 6 mg |
| vitamin B6 (pyridoxine) | 2 mg |
| arginine | 500 mg |
| vitamin C | 90 mg |
| vitamin E (α-Tocopherolo) | 30 mg |
| selenium | 50 mcg |
| zinc | 10 mg |
| copper | 1.65 mg |
| iron | 14 mg |
| vitamin D | 5 mcg |
| N-acetyl cysteine | 50 mg. |

| Composition 3 | |
|---|---|
| L-carnitine fumarate | 863 mg |
| acetyl-L-carnitine | 125 mg |
| folic Acid (vitamin B9) | 200 mcg |
| vitamin A from Beta Carotene | 800 mcg |
| vitamin B12 | 2.5 mcg |
| vitamin B5 (pantothenic) | 6 mg |
| vitamin B6 (pyridoxine) | 2 mg |
| arginine | 500 mg |
| vitamin C | 90 mg |
| vitamin E (α-Tocopherolo) | 30 mg |
| selenium | 50 mcg |
| zinc | 10 mg |
| copper | 1.65 mg |
| iron | 14 mg |
| vitamin D | 5 mcg |
| N-acetyl cysteine | 50 mg. |

| Composition 4 | |
|---|---|
| L-carnitine fumarate | 430 mg |
| acetyl-L-carnitine | 250 mg |
| folic Acid (vitamin B9) | 200 mcg |
| vitamin A from Beta Carotene | 800 mcg |
| vitamin B12 | 2.5 mcg |
| vitamin B5 (pantothenic) | 6 mg |
| vitamin B6 (pyridoxine) | 2 mg |
| arginine | 500 mg |
| vitamin C | 90 mg |
| vitamin E (α-Tocopherolo) | 30 mg |
| selenium | 50 mcg |
| zinc | 10 mg |
| copper | 1.65 mg |
| iron | 14 mg |
| vitamin D | 5 mcg |
| N-acetyl cysteine | 50 mg. |

The invention claimed is:

1. A combination composition comprising as active ingredients: L-carnitine or a salt thereof in a dose of from 2589 to 287.6 mg (corresponding to 1500-166.6 mg L-carnitine inner salt), acetyl L-carnitine or a salt thereof in a dose of from 750 to 25.0 mg, vitamin B9 (folic Acid) in a dose of from 600 to 66.6 µg, vitamin A in a dose of from 2400 to 266.6 µg, vitamin B12 in a dose of from 7.5 to 0.833 µg, vitamin B5 (pantothenic acid) in a dose of from 18.0 to 2.0 mg, vitamin B6 (pyridoxine) in a dose of from 6.0 to 0.666 mg, arginine in a dose of from 1500 to 166.6 mg, vitamin C in a dose of from 270.0 to 30.0 mg, vitamin E (α-Tocopherol) in a dose of from 90.0 to 10.0 mg, selenium in a dose of from 150 to 16.6 µg, zinc in a dose of from 30.0 to 3.33 mg, copper in a dose of from 4.95 to 0.55 mg, iron in a dose of from 42.0 to 4.66 mg, vitamin D in a dose of from 15.0 to 1.66 µg and N-acetyl cysteine in a dose of from 150 to 16.6 mg, and optionally one or more pharmaceutically acceptable excipients.

2. The combination composition of claim 1, further comprising co-enzymes, mineral substances, antioxidants, and vitamins.

3. A dietary supplement comprising the combination composition of claim 1.

4. The combination composition of claim 1, in which the salt of L-carnitine or acetyl L-carnitine is selected from the group consisting of chloride, bromide, orotate, aspartate, citrate, phosphate, fumarate, lactate, maleate, oxalate, pamoate, sulphate, tartrate and mucate.

5. The combination composition of claim 1, for oral administration.

6. The combination composition of claim 1, which comprises:
L-carnitine fumarate in a dose of from 1726 to 431.5 mg (corresponding to 1000-250 mg of L-carnitine inner salt);
Acetyl L-carnitine in a dose of from 500 to 125 mg;
folic acid (vitamin B9) in a dose of from 400 to 100 µg;
vitamin A from beta carotene in a dose of from 1600 to 400 µg;
vitamin B12 in a dose of from 5.0 to 1.250 µg;
vitamin B5 (pantothenic) in a dose of from 12.0 to 3.0 mg;
vitamin B6 (pyridoxine) in a dose of from 4.0 to 1.0 mg;
arginine in a dose of from 1000.0 to 250.0 mg;
vitamin C in a dose of from 180.0 to 45.0 mg;
vitamin E (α-Tocopherol) in a dose of from 60.0 to 15.0 mg;
selenium in a dose of from 100.0 to 25.0 µg;
zinc in a dose of from 20.0 to 5.0 mg;
copper in a dose of from 3.3 to 0.825 mg;
iron in a dose of from 28.0 to 7.0 mg;
vitamin D in a dose of from 10.00 to 2.50 µg; and
N-acetyl cysteine in a dose of from 100.0 to 25.0 mg.

7. The combination composition of claim 6, which comprises:
L-carnitine fumarate in a dose of 863 mg (corresponding to 500 mg of L-carnitine inner salt);
Acetyl L-carnitine in a dose of 250 mg;
folic acid (vitamin B9) in a dose of 200 µg;
vitamin A from beta carotene in a dose of 800 µg;
vitamin B12 in a dose of 2.5 µg;
vitamin B5 (pantothenic) in a dose of 6 mg;
vitamin B6 (pyridoxine) in a dose of 2 mg;
arginine in a dose of 500 mg;
vitamin C in a dose of 90 mg;
vitamin E (α-Tocopherol) in a dose of 30 mg;
selenium in a dose of 50 µg;
zinc in a dose of 10 mg;
copper in a dose of 1.65 mg;
iron in a dose of 14 mg;
vitamin D in a dose of 5 µg; and
N-acetyl cysteine in a dose of 50 mg.

8. A method of promoting female fertility, the method comprising administering the combination composition of claim 1 to a women in need thereof.

9. A method of promoting female fertility during drug stimulation, hormonal stimulation, or drug and hormonal stimulation, the method comprising administering the combination composition of claim 1 to a women in need thereof.

10. A method of promoting female fertility during drug stimulation, hormonal stimulation, or drug and hormonal stimulation for supporting ovulation, the method comprising administering the combination composition of claim 1 to a women in need thereof.

11. The method of claim 10, in which the administration of the combination composition is started at least a month before the beginning of the drug stimulation, hormonal stimulation, or drug and hormonal stimulation.

12. The method of claim 10 in which the administration of the combination composition is started at least a week before the beginning of the drug stimulation, hormonal stimulation, or drug and hormonal stimulation.

13. A method of promoting female fertility during during drug stimulation, hormonal stimulation, or drug and hormonal stimulation for promoting oocyte fertilization, the method comprising administering the combination composition of claim 1 to a women in need thereof.

14. A method of promoting female fertility during drug stimulation, hormonal stimulation, or drug and hormonal stimulation for promoting oocyte fertilization in vivo, the method comprising administering the combination composition of claim 1 to a women in need thereof.

15. A method of promoting female fertility during drug stimulation, hormonal stimulation, or drug and hormonal stimulation for promoting oocyte fertilization in vitro, the method comprising administering the combination composition of claim 1 to a women in need thereof.

16. A method of reducing side effects due to the use of hormones, drugs, or hormone and drugs useful for promoting female fertility, the method comprising administering the combination composition of claim 1 to a women in need thereof.

* * * * *